(12) United States Patent  
Ogihara et al.

(10) Patent No.: US 7,027,139 B2
(45) Date of Patent: Apr. 11, 2006

(54) PHOTOSENSOR APPARATUS AND IMAGE FORMING APPARATUS

(75) Inventors: Atsushi Ogihara, Kanagawa (JP);
Kunio Yamada, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 106 days.

(21) Appl. No.: 10/868,961

(22) Filed: Jun. 17, 2004

(65) Prior Publication Data

US 2005/0083530 A1    Apr. 21, 2005

(30) Foreign Application Priority Data

Oct. 22, 2003    (JP)    ............................ P2003-362012

(51) Int. Cl.
    *G01N 21/47*    (2006.01)
    *G03G 15/00*    (2006.01)
    *H04N 1/00*    (2006.01)

(52) U.S. Cl. ........................ 356/218; 356/446; 399/46; 399/49; 358/488; 358/446

(58) Field of Classification Search ........ 356/213–235, 356/445–448; 339/46, 49, 301, 74; 358/488, 358/406, 509, 446; 382/32, 65
See application file for complete search history.

(56) References Cited

U.S. PATENT DOCUMENTS

| | | | | |
|---|---|---|---|---|
| 5,367,379 A | * | 11/1994 | Makino | ........................ 356/446 |
| 5,404,156 A | * | 4/1995 | Yamada et al. | ............. 347/115 |
| 5,652,655 A | * | 7/1997 | Uno et al. | ................... 356/600 |
| 5,729,786 A | * | 3/1998 | Yamada et al. | ................ 399/42 |
| 5,764,380 A | * | 6/1998 | Noguchi | ...................... 358/488 |
| 6,122,075 A | * | 9/2000 | Yamada et al. | ............. 358/446 |
| 6,169,612 B1 | * | 1/2001 | Deguchi | ...................... 358/488 |
| 6,633,734 B1 | * | 10/2003 | Maebashi et al. | ............. 399/49 |
| 6,937,826 B1 | * | 8/2005 | Yamamoto et al. | ........... 399/49 |

FOREIGN PATENT DOCUMENTS

| | | | |
|---|---|---|---|
| JP | 63205588 A | * | 8/1988 |
| JP | 63304275 A | * | 12/1988 |
| JP | A-2000-047447 | | 2/2000 |
| JP | A-2000-250304 | | 9/2000 |
| JP | A-2002-244371 | | 8/2002 |

* cited by examiner

*Primary Examiner*—Samuel A. Turner
*Assistant Examiner*—Sang H. Nguyen
(74) *Attorney, Agent, or Firm*—Morgan Lewis & Bockius LLP

(57) ABSTRACT

A photosensor apparatus includes a light receiving element that receives reflection light of light which is illuminated onto a reference pattern image formed on a moving member, a first illuminating unit that enters regular reflection light to the light receiving element, a second illuminating unit that enters diffuse reflection light to the light receiving element, and a light receiving optical system that conducts the regular reflection light and the diffuse reflection light to the light receiving element. Preferably, the light receiving optical system includes a lens, constitutes an image forming optical system that forms the reference pattern image on a light receiving plane of the light receiving element with respect to the diffuse reflection light, and enters to the light receiving plane of the light receiving element only a part of regular reflection light, which is reflected from substantially the same region where the diffuse reflection light is received.

16 Claims, 9 Drawing Sheets

PHOTOSENSOR APPARATUS AND IMAGE FORMING APPARATUS

BACKGROUND OF THE INVENTION

1. Field of the Invention

The present invention is related to a technique for detecting a forming position of an output image in an image forming apparatus such as a copying machine and a printer and for adjusting an image forming position based upon the detection result, and also related to a technique for detecting photographic density, colors, and gradation of an output image in the image forming apparatus and for controlling an image forming condition based upon the detection results.

2. Description of the Related Art

Image qualities of image forming apparatus are conspicuously improved, and in connection with this image quality improvement, sever requirements are made by users with respect to variations in image qualities of color images. As a result of investigation made by the Inventors, such image qualities near limitations of human color discriminating capabilities are required, for instance, a color difference lower than, equal to 3 is required. Also, sever requirements with respect to color shifts are made by users, for example, color shifts must be lower than, or equal to 100 to 200 μm.

In particular, among electrophotographic type color image forming apparatus and the like, which have employed electrophotographic processes, variations in image qualities known as image density, positional shifts of respective color toner images, color reproducibilities, gradient characteristics, and photographic fog, may constitute problems to be solved. In such an electrophotographic type color image forming apparatus, while an electrostatic latent image is formed on a photosensitive member, this electrostatic latent image is developed by a toner so as to form a toner image on the photosensitive member, and then, this toner image is directly transferred to a recording medium, or is transferred via an intermediate transfer member to the recording medium, and thereafter, this transferred toner image is fixed on the recording medium. This problem is mainly caused by that an image quality reproducibility of an electrophotographic process is adversely influenced by such an environmental condition as a temperature and humidity, and also deteriorations by aging effects.

With respect to the above-described problem, such an image forming system has been widely used in which reflection light of light illuminated to an image quality controlling reference pattern image formed on an image carrier is sensed by an optical type photosensor so as to perform both an image density adjusting operation and a positional adjusting operation based upon the sensor output. Another image forming apparatus has been proposed (JP-A-2000-47447). In this image forming apparatus, while both density changes and positional shift amounts of reference pattern images in yellow, magenta, cyan colors are detected by a photosensor, which have been formed on a image carrier, both the image forming density and the positional shift are controlled every color component based upon this detection result. In addition, as the photosensor, such a photosensor apparatus used in an image forming apparatus has been proposed (JP-A-2000-250304). That is, while both a regular reflection type and a diffuse reflection type are combined to be conducted to a photosensor apparatus, this photosensor apparatus is applied to the image forming apparatus so as to control both image forming density and a positional shift. In the regular reflection type photosensor, regular reflection light reflected from a black toner image is sensed, and thus, density is detected in a higher sensitivity. In the diffuse reflection type photosensor, while diffuse reflection light reflected from the respective reference pattern images is sensed, density up to high density can be detected.

On the other hand, when density is detected by employing a photosensor, there is such a problem. That is, a wide detecting visual field with respect to diffuse reflection light where reflection light is diffused must be secured, as compared with a detecting visual field when regular reflection light is detected. As a consequence, in a conventional sensor optical system, sizes of reference pattern images for yellow, magenta, and cyan colors, which reflects light in a diffuse reflection mode, cannot be made smaller than a size of a reference pattern image for a black color, which reflects light in a regular reflection mode. As a result, there is such a drawback that in order to form the above-described reference pattern images for these three colors, a larger amount of toners are required, as compared with an amount of toners used to form the reference pattern image for the black color, and furthermore, extra toners are consumed so as to perform adjusting process operation.

Further, another method has been proposed by employing a single photosensor in order also detect a position (registration detection) However, even in such a case that a diffuse system is employed by which an adverse influence of a mounting angle error of the photosensor is reduced, since a visual field required to detect diffuse reflection light becomes wide, there is another problem that position detecting precision is deteriorated. As a consequence, a requirement of such a technical idea has been made, by which the visual field required to detect the diffuse reflection light may be made substantially equal to the visual field required to detect the regular reflection light.

In response to this requirement, another method has been proposed (JP-A-2002-244371). This proposed method limits the visual fields with respect to the diffuse reflection system and the regular reflection system. However, in such a case that this proposed method is applied, two sorts of sensors are required, namely, both the diffuse reflection-purpose sensor and the regular reflection-purpose sensor are required, so that total cost of these sensors becomes twice. Furthermore, in such a case that these two sorts of sensors are simply combined with each other, two sorts of light receiving optical systems corresponding to both the diffuse reflection light and the regular reflection light are required. This may cause the complex structure of the photosensor apparatus, and the cost reducing effect would be decreased.

SUMMARY OF THE INVENTION

The present invention has been made to solve the above-described problems, and therefore, provides a compact photosensor apparatus capable of reducing cost. That is in the photosensor apparatus, both diffuse reflection light and regular reflection light are sensed by a single light receiving element, the photosensor apparatus can function as a density sensor and a position sensing sensor, and since the respective reflection light is limited to visual field sizes having the same sizes, a toner amount used to form a reference pattern image can be reduced.

The present invention has been made in view of the above circumstances and provides a photosensor apparatus including a light receiving element that receives reflection light of light which is illuminated onto a reference pattern image formed on a moving member, a first illuminating unit that is disposed at a first position so that regular reflection light of light from the first illuminating unit by the reference pattern image enters to the light receiving element a second illuminating unit that is disposed at a second position so that diffuse reflection light of light from the second illuminating unit by the reference pattern image enters to the light receiving element, and a light receiving optical system that conducts the regular reflection light and the diffuse reflection light generated at the reference pattern image to the light receiving element. Preferably, the light receiving optical system includes a lens, constitutes an image forming optical system that focuses the reference pattern image on a light receiving plane of the light receiving element with respect to the diffuse reflection light, and enters only a part of regular reflection light to the light receiving plane of the light receiving element with respect to the regular reflection light, the part of regular reflection light being reflected from substantially the same region where the diffuse reflection light is received by the light receiving element within the reference pattern image on the moving member.

In such a photosensor apparatus of the present invention, the light receiving element may sense both the regular reflection light and the diffuse reflection light, namely, may sense light which is entered into the light receiving plane thereof. Then, the right receiving element may preferably own such a light receiving plane having a size capable of sufficiently storing therein a subject region where the respective reflection light is received to the light receiving plane of this light receiving element.

In order that the above-described photosensor apparatus plays a role as both a density sensing function and a positional shift sensing function, the photosensor apparatus requires both the first illuminating unit and the second illuminating unit, which enter both the regular reflection light and the diffuse reflection light into the light receiving element. The illuminating unit may be preferably constructed of such a light emitting element as an LED, which emits such a light. That is, when a reference pattern image formed on the moving member is illuminated by this light, such a reflection light can be obtained which can be sensed by the light emitting element.

In this time, in such a case that either the density detecting reference pattern images of the three colors (yellow, magenta, cyan) or the position adjusting-purpose reference pattern images for the three colors are illuminated by the second illuminating unit, which have been formed on the moving member, the diffuse reflection light is entered into the light receiving optical system. At this time, it is preferable that the light receiving optical system constitutes an image forming optical system. In this image forming optical system, the density sensing-purpose reference pattern image and the position adjusting-purpose reference pattern image are imaged onto the light receiving plane. That is to say, in order to focus these reference pattern images, a lens may be preferably arranged between the moving member and the light receiving element. Then, as to the arranging position of the lens and the optical specification thereof, any kinds of lenses may be employed, if these lenses can focus the reference pattern images formed on the moving member on the light receiving plane. In this construction, since the respective reference pattern image may be imaged on the light receiving plane under focusing condition, these reference pattern images can be detected in high precision.

In the image forming optical system into which the diffuse reflection light, such a diffuse reflection light which is not required for either the density sensing operation or the position adjusting operation is entered from a peripheral portion of the reference pattern image in addition to the above-explained diffuse reflection light which becomes effective in either the density sensing operation or the position adjusting operation and is entered from the reference pattern image. At this time, in such a case that this unnecessary diffuse reflection light is also sensed by the photosensor, noise is also mixed in the sensing signal, so that the detection precision is lowered. As a consequence, such a mask may be preferably provided which may shield the unnecessary diffuse reflection light and also may restrict the detection region of the light receiving plane. The small reference pattern image can be detected by the visual field region of the narrow light receiving plane by way of this mask, and thus, the toner amount used to form this reference pattern image can be reduced. It should be noted that the above-described mask may be preferably made of a black-colored plate member in order to prevent stray light. Then, a hole which is pierced in this mask may be preferably a circle, and a diameter of this hole may be properly set in response to a region of such a reflection light which should be conducted to the light receiving plane.

On the other hand, in such a case that the reference pattern image for sensing the density of the black toner is illuminated by the first illuminating unit, the regular reflection light is entered to the light receiving optical system. In this case, the light receiving optical system may be preferably arranged in such a manner that this light receiving optical system may receive only such regular reflection light which is located substantially parallel to each other, and is emitted from the light receiving subject region. In this structure, the density sensing-purpose reference pattern image is not required to be focused on the light receiving plane, but may have such a size larger than, or equal to the size of the light receiving subject region. Under such a reason, as the lens of this optical system, such a lens having optical magnification of 1:1 (1 time) may be preferably utilized. Also, in this optical system, since it is sufficient that a least necessary light amount of the regular reflection light for detecting the density of the black toner can be conducted to the light receiving plane, this optical system may be alternatively constructed in such a manner that only such a regular reflection light component having luminous intensity which becomes effective in the density sensing operation can be conducted to the light receiving plane. With employment of this structure, the reference pattern image can be set to be a small size, but also the size of the reference pattern image can be made equal to the size of the image forming optical system. In addition, a total amount of toners which are used to sense the density of the black toner can be saved.

On the other hand, the light receiving element senses both the density and the positional shift based upon a difference between a reference voltage value and an output voltage value of this light receiving element, which is caused by entering reflection light to the light receiving element. As a result, when the density is sensed, such a light which constitutes a reference (will be referred to as "reference light" hereinafter) is required to be entered into the light receiving plane. Under such a condition, a reference plate capable of reflecting this reference light may be preferably provided. As this method, either before the sensing operation is carried out or after the sensing operation is carried out, either the first illuminating unit or the second illuminating unit may illuminate the illumination light to this reference plate. It is preferable to construct such a movable mechanism in such a manner that either the first illuminating unit or the second illuminating unit may illuminate the illumination light to the reference pattern image during the sensing operation.

As previously explained, since the density sensing-purpose reference pattern images for the three colors (yellow, magenta, cyan) can be sensed by arranging an image forming optical system, the photosensor apparatus of the present invention may be alternatively applied to a color image forming apparatus.

[Effects of the Invention]

In accordance with the photosensor apparatus of the present invention which has been constructed in the above-described manner, not only the function as the density sensor and the function as the position sensing sensor can be realized by employing a single light receiving element, but also the visual field sizes on the light receiving planes of the light receiving elements in the respective optical systems can be restricted to the same sizes. As a consequence, the toner amount used to form the reference pattern images can be reduced, and thus, the photosensor apparatus can be made compact as well as the manufacturing cost can be reduced.

BRIEF DESCRIPTION OF THE DRAWINGS

Preferred embodiment of the present invention will be described in detail based on the following figures, wherein.

DETAILED DESCRIPTION OF THE INVENTION

A detailed description is made of such an embodiment case that a photosensor apparatus of the present invention is applied to an image forming apparatus based upon the attached drawings.

Figure 1:
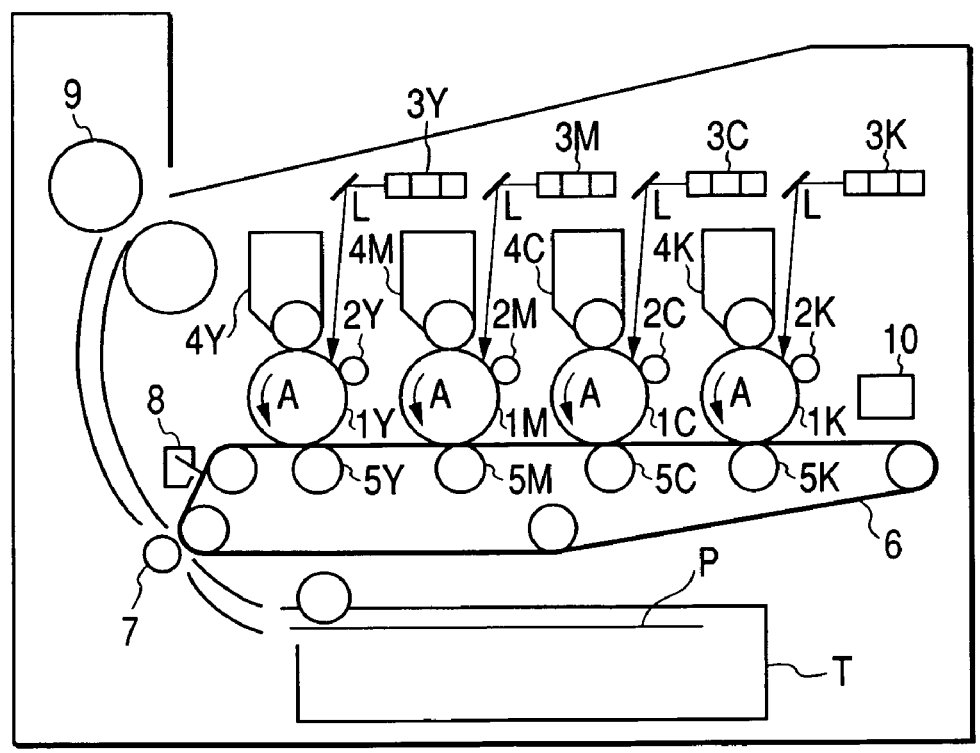
FIG. 1 is a schematic structural diagram of an image forming apparatus to which a photosensor apparatus of the present invention is applied.

FIG. 1 is a schematic structural diagram of a color image forming apparatus using an electrophotographic system to which the present invention is applied. This structural diagram indicates an outline of an IOT (Image Output Terminal) of a tandem type color electrophotographic system of an image forming apparatus. The image forming apparatus is equipped with xerography engines as to respective colors, namely yellow, magenta, cyan, and black. In these color xerographic engines, after surfaces of photosensitive members have been charged by contact charging devices, electrostatic latent images are formed on these charged surfaces by irradiating laser light, and then, the electrostatic latent images are developed by using toners. It should be noted that an image reading unit and an image processing unit of the image forming apparatus are omitted in this drawing.

The IOT of this image forming apparatus is constituted by four photosensitive members 1Y, 1M, 1C, 1K; contact charging devices 2Y, 2M, 2C, 2K; ROSs (Raster Output Scanner=laser output units) 3Y, 3M, 3C, 3K; developing devices 4Y, 4M, 4C, 4K; primary transferring devices 5Y, 5M, 5C, 5K; a secondary transferring device 7; a fixing device 9; a paper tray T; a cleaner (not shown) an electric eliminator (not shown); a photosensor 10, and a belt cleaner 8. The photosensitive members 1Y, 1M, 1C, 1K are rotated along a direction indicated by symbol A in this drawing. The contact charging devices 2Y, 2M, 2C, 2K charge surfaces of the respective photosensitive members. The ROSs (laser output units) 3Y, 3M, 3C, 3K expose the charged surfaces of the respective photosensitive members by using exposure light which is modulated based upon image information as to the respective colors so as to form electrostatic latent images on the respective photosensitive members. The developing devices 4Y, 4M, 4C, 4K develop the electrostatic latent images on the respective photosensitive members by using respective color developing agent so as to form toner images on the photosensitive members. The primary transferring devices 5Y, 5M, 5C, 5K transfer the respective color toner images formed on the photosensitive members to an intermediate transfer member belt 6. The secondary transferring device 7 transfers the toner images on the intermediate transfer member belt 6 to a paper P. The fixing device 9 fixes the toner image which has been transferred to the paper P. The paper tray T stores thereinto the paper P. The cleaner cleans the surfaces of the respective photosensitive members. The electric eliminator electrically eliminates residual charges on the surfaces of the respective photosensitive members. The photosensor 10 senses both a reference pattern image used for image density control operation and a reference pattern image used for image forming position adjusting operation, which have been transferred to the surface of the intermediate transfer member belt 6. The belt cleaner 8 cleans the surface of the intermediate transfer member belt 6.

As an image forming operation executed in the image forming apparatus shown in this drawing, first of all, either an original image signal read out from an original by an image reading unit (not shown) or an original image signal formed in an external computer (not shown) and the like is entered into an image processing unit (not shown). This input image signal is subdivided into image information of the respective colors, and thereafter, the image information is inputted to the ROSs (laser output units) 3Y, 3M, 3C, 3K, respectively, so that laser light L is modulated by these color image data. Then, this modulated laser light L is irradiated onto the surfaces of the photosensitive members 1Y, 1M, 1C, 1K which have been uniformly charged by the contact charging devices 2Y, 2M, 2C, 2K. When the laser light L is irradiated onto the surfaces of the respective photosensitive members 1Y, 1M, 1C, 1K in a raster mode, electrostatic latent images corresponding to the respective input image signals are formed on the respective photosensitive members. Subsequently, the electrostatic latent images formed on the respective photosensitive members 1Y, 1M, 1C, 1K are developed by the respective color developing devices 4Y, 4M, 4C, 4K, so that toner images are formed on the respective photosensitive members 1Y, 1M, 1C, 1K. The toner image formed on the respective photosensitive members 1Y, 1M, 1C, 1K are transferred to the intermediate transfer member belt 6 by the respective primary transferring devices 5Y, 5M, 5C, 5K. In each of the photosensitive members 1Y, 1M, 1C, 1K where the transfer operations of the toner images to this intermediate transfer belt 6 have been accomplished, adhesive articles such as remaining toners which are adhered to the surface thereof are cleaned by the cleaner, and residual electric charges are eliminated by the electric eliminator.

Next, after the toner images on the intermediate transfer member belt 6 are transferred onto the paper P fed from the paper tray T, the toner images which have been transferred to the paper P are fixed by the fixing device 9, so that a desirable image is obtained. In the intermediate transfer member belt 6 in which the transfer operations of the toner images to the paper P are accomplished, adhesive articles such as remaining toners which have been adhered to the surface thereof are cleaned by the belt cleaner 8, so that a single image forming operation is completed.

In an electrophotographic type color image forming apparatus, such image variations as image density, positional shifts of the respective color toner images, color reproducibility, gradient characteristic, and photographic fog may occur due to such adverse influences as environmental conditions (temperature, humidity etc.) and aging effects. As a result, image density adjusting operation and image position adjusting operation must be carried out before images are outputted to the paper P, or under output waiting condition of images. As this adjusting method, first, a reference pattern image used for adjusting image density and also a reference pattern image for adjusting an image position are formed. Then, these reference patterns are detected by the photosensor 10, so that detection output signals are sent to a control unit. Furthermore, as a result of a density variation and a positional shift amount, which are obtained from this detection output signal, both the image density adjusting operation and the image position adjusting operation are carried out, if necessary.

Figure 2:
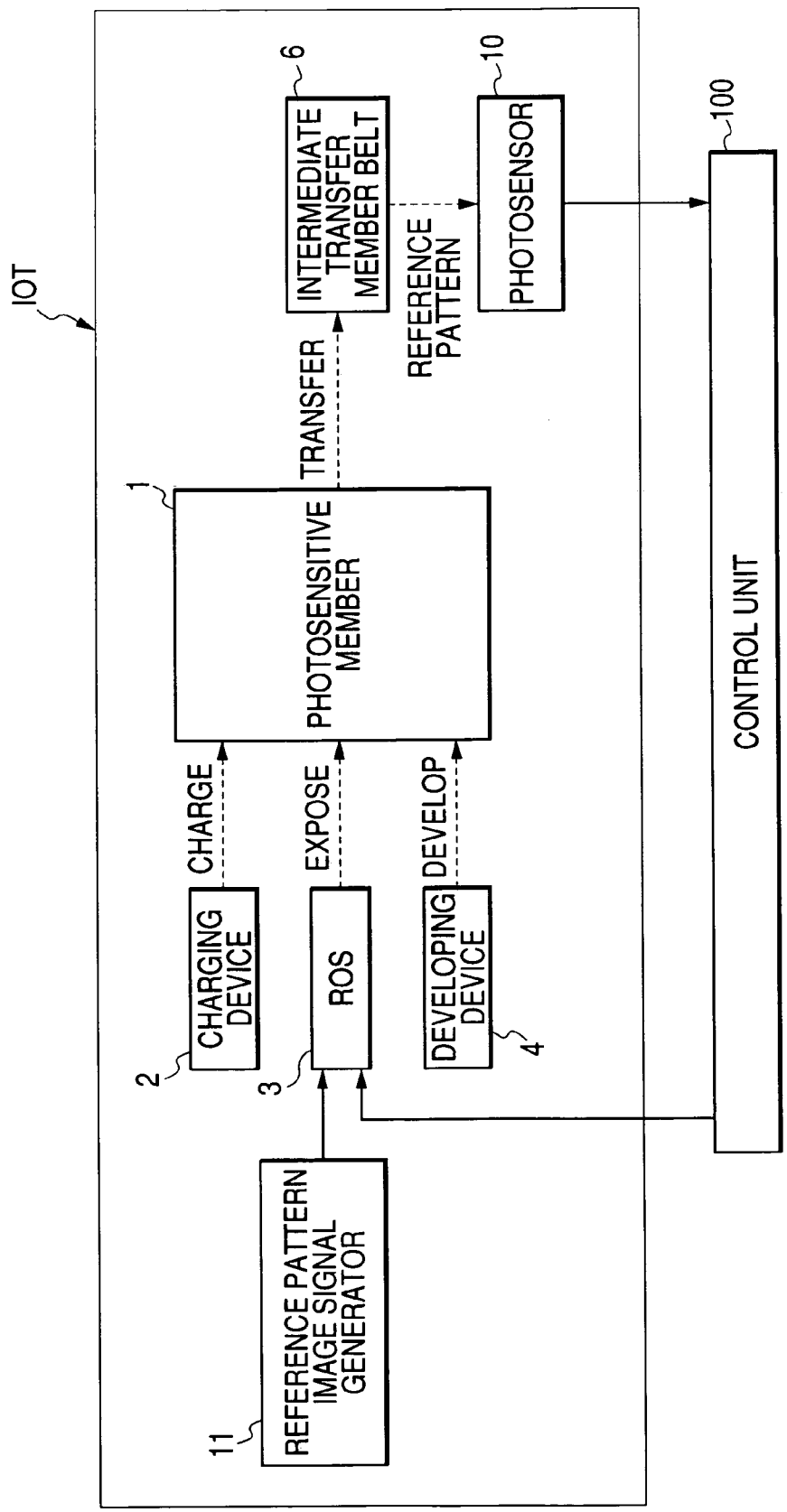
FIG. 2 is a functional block diagram of the image forming apparatus of FIG. 1.

FIG. 2 is a block diagram for representing a flow operation with respect to both an image density adjusting operation and an image position adjusting operation, which are executed in the color image forming apparatus shown in FIG. 1. A photosensitive member 1 is charged by a contact charging device 2, and the photosensitive member 1 is exposed by an ROS 3 in response to a reference pattern image signal outputted from a reference pattern signal image signal generator 11, so that an electrostatic latent image. After this electrostatic latent image has been developed by a developing device 4, the developed reference pattern image is transferred onto an intermediate transfer member belt 6. Then, the reference pattern image which has been transferred onto the intermediate transfer member belt 6 is detected by a photosensor 10.

A control unit 100 controls laser power of the ROS 3 in response to an output signal derived from the photosensor 10 so as to adjust image density. Also, the control unit 100 controls writing timing of the ROS 3 in response to the output signal derived from the photosensor 10 in order to adjust an image forming position.

Figure 3A:
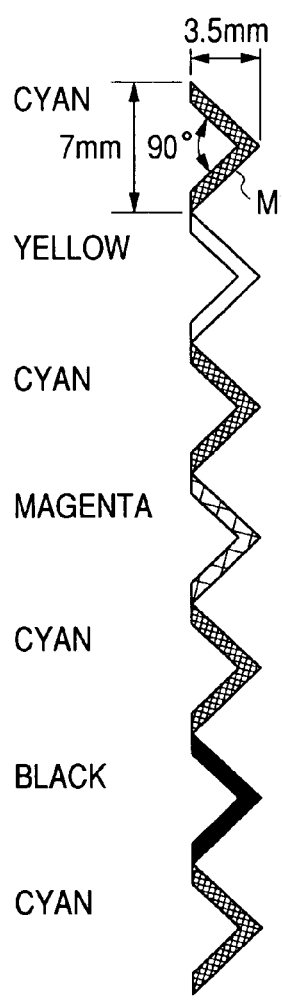
FIGS. 3A and 3B are plan views for indicating an image density controlling reference pattern and an image forming position adjusting-purpose reference pattern.
Figure 3B:
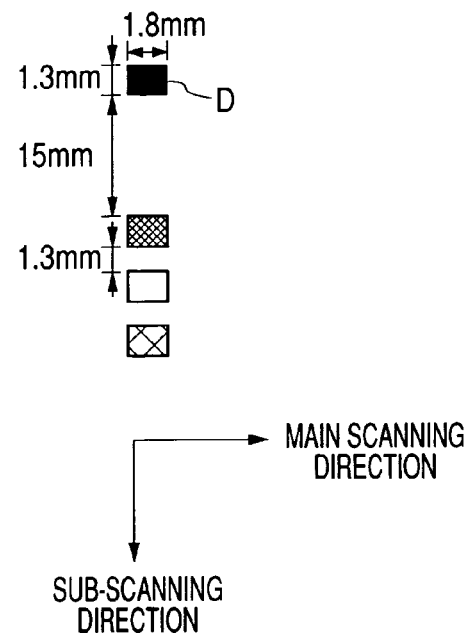

FIGS. 3A and 3B are arranging diagrams of the reference pattern image which is formed on the intermediate transfer member belt 6. In this embodiment, two sorts of reference pattern images are employed, namely, a reference pattern image M used for adjusting an image forming position (see FIG. 3A), and a reference pattern image D used for controlling image density (see FIG. 3B) are employed. The image forming position adjusting-purpose reference pattern image M employs such a pattern image that plural monochromatic V-shaped pattern images each having a size of 3.5 mm×7 mm of mesh point coverage: Cin=100% are arranged in this order of cyan, yellow, cyan, magenta, cyan, black, and cyan. The image density controlling reference pattern image D employs such a pattern image that plural monochromatic rectangular-shaped pattern images each having a size of 1.8 mm×1.3 mm of mesh point coverage: Cin=60% are arranged in this order of black, cyan, yellow, and magenta, while intervals among the respective pattern images are defined as 15 mm, 1.3 mm, and 1.3 mm. Each of the reference pattern images is formed during a position adjusting operation and a density control operation respectively.

Figure 4:
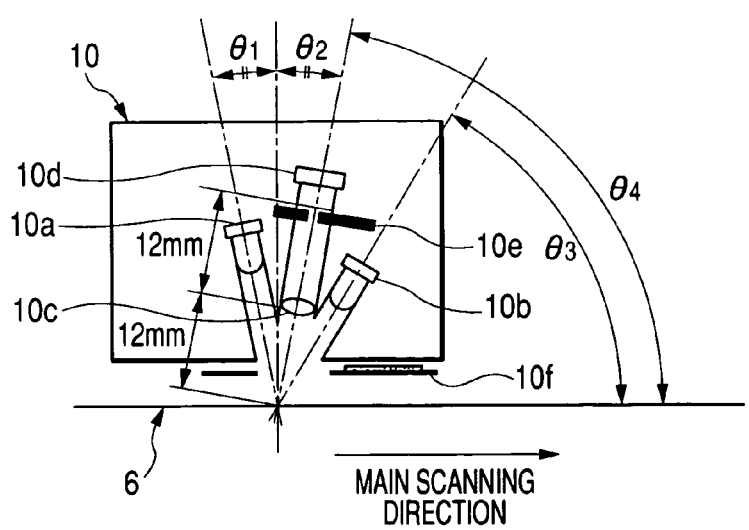
FIG. 4 is a schematic structural diagram of a photosensor.
Figure 5:
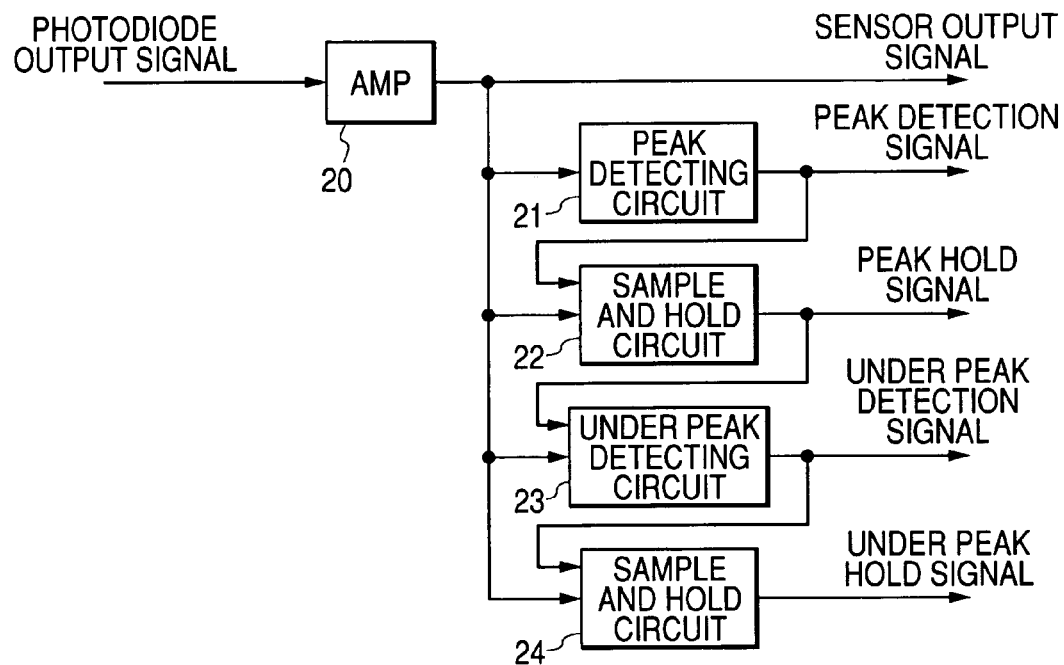
FIG. 5 is a block diagram for showing a flow of output signals from a photodiode in a photosensor which is arranged by an AMP, a peak detecting circuit, an under peak detecting circuit, and two sets of sample and hold circuits.

FIG. 4 is a schematic structural diagram of the photosensor 10 employed in this embodiment. This photosensor 10 is constructed of an illuminating unit, a light receiving optical system, and a light receiving element. The illuminating unit is arranged by two sorts of illuminating units, namely, a regular reflection-purpose LED 10a and a diffuse reflection-purpose LED 10b. Then, the light receiving optical system is constituted by a lens 10c and a mask 10e. In this drawing, right and left directions correspond to a main scanning direction. Also, FIG. 5 is a block diagram for indicating a flow operation of an output signal from a photodiode 10d. This flow diagram is arranged by an AMP (amplifier), a peak detecting circuit, an under peak detecting circuit, and two sets of sample and hold circuits. These circuits are contained in the control unit 100 shown in FIG. 2.

In order to sense both a positional shift and a density variation by using the photosensor 10, both the image forming position adjusting-purpose reference pattern image M shown in FIG. 3A, and the image density controlling reference pattern image D indicated in FIG. 3B are required to be illuminated by the illuminating unit. For example, in such a case that the density variation is sense, as previously explained, the image density controlling reference pattern image D in which the respective monochromatic pattern images are arranged in this order of black, cyan, yellow, and magenta colors is illuminated by the illuminating unit. However, as to reflection light reflected from the black reference pattern image, a light amount of regular reflection light is large whereas a light amount of diffuse reflection light is small. Then, as to reflection light reflected from the cyan reference pattern image, the yellow reference pattern image, and the magenta reference pattern image, a light amount of regular reflection light is small whereas a light amount of diffuse reflection light is large. As a consequence, in order to sense these two sorts of reflection light by using a single light receiving element (photodiode 10d), the above-explained reference pattern images must be illuminated onto this single light receiving element from positions into which both the regular reflection light and the diffuse reflection light can be entered, so that two sets of illuminating units are required.

In order to enter the regular reflection light into the photodiode 10d, both the regular reflection-purpose LED 10a and the photodiode 10d may be arranged in such a positional relationship that the regular reflection light caused by illuminating the light to the reference pattern image can be received by the photodiode 10d. In this example, it is so assumed that an angle is equal to "$\theta_1$", which is defined between a normal line located perpendicular to the surface of the intermediate transfer member belt 6 and an optical axis of illumination light emitted from the regular reflection-purpose LED 10a. Also, it is so assumed that an angle is equal to "$\theta_2$", which is defined between the normal line located perpendicular to the surface of the intermediate transfer member belt 6 and an optical axis of incident light entered into the photodiode 10d. At this time, it is preferable that both the regular reflection-purpose LED 10a and the photodiode 10d are arranged in such a positional relationship of $\theta_1=\theta_2$. In the photosensor 10, since the regular reflection-purpose LED 10a and the photodiode 10d are arranged in such a positional relationship of $\theta_1=\theta_2=10$ degrees, the regular reflection light produced while the reference pattern image is illuminated by the regular reflection-purpose LED 10a can be entered to the photodiode 10d.

Next, similar to the above-described case of the regular reflection light, in order to enter the diffuse reflection light into the photodiode 10d, both the diffuse reflection-purpose LED 10b and the photodiode 10d may be preferably arranged in such a positional relationship that the diffuse reflection light can be received by the photodiode 10d. In this example, it is so assumed that an angle defined between the diffuse reflection-purpose LED 10b and the surface of the intermediate transfer member belt 6 is equal to "$\theta_3$", and another angle defined between an optical axis of incident light entered into the photodiode 10d is equal to "$\theta_4$". At this time, both the diffuse reflection-purpose LED 10b and the photodiode 10d may be arranged under such a condition that a positional relationship of "$\theta_3<\theta_4$" may be satisfied. In the photosensor 10, the angles are set as follows: $\theta_3=60$ degrees and $\theta_4=80$ degrees, which can satisfy such a positional relationship of "$\theta_3<\theta_4$". As a consequence, the diffuse reflection light of the reference pattern image emitted from the diffuse reflection-purpose LED 10b can be entered to the photodiode 10d.

As the lens 10c of the light receiving optical system, such a lens having a diameter of 3 mm and a focal distance of 6 mm. Both a distance from the surface of the intermediate transfer member body 6 up to the lens 10c, and a distance from the lens 10c up to the photodiode 10d are equal to each other, namely 12 mm. Optical magnification is set to 1 time. Since this arrangement is employed, an image forming optical system having the optical magnification of 1 time may be constructed with respect to the diffuse reflection light produced when the diffuse-purpose LED 10b is illuminated.

In the above-described image forming optical system, while the reference pattern image projected by the diffuse reflection light is focused on the light receiving plane of the photodiode 10d, such a diffuse reflection light which is unnecessary for density sensing operation and positional adjusting operation is also received, so that the unnecessary diffuse reflection light is required to be shielded. Also, in order to sense density of a black toner, only such a light component of the effective regular reflection light may be conducted to the light receiving plane of the photodiode 10d. As a consequence, in order to satisfy the above-explained two conditions, a mask 10e is provided just before the photodiode 10d, and this mask 10e restricts a visual field region of the light receiving plane of this photodiode 10d. A hole of the mask 10e is made of a circular having a diameter of 1 mm, and a mask portion other than this hole of the mask 10e is colored in a black color so as to prevent stray light. As a result, in any case of both the regular reflection light and the diffuse reflection light, the visual field region of the light receiving plane of the photodiode 10d can be made substantially equal to the hole of the mask 10e, namely a diameter of 1 mm.

When reflection light reflected from a reference pattern image is projected onto the light receiving plane of the photodiode 10d, the photodiode 10d outputs a current which is defined in response to a light amount of this reflection light, namely a shade of the reference pattern image. As indicated in FIG. 5, the current outputted from the photodiode 10d is converted into a corresponding voltage signal and this voltage signal is amplified by the AMP 20, and thereafter, the amplified voltage signal is supplied as a sensor output signal to a control unit (not shown), a peak detecting circuit 21, an under peak detecting circuit 23, and two sets of sample and hold circuits 22 and 24.

The peak detecting circuit 21 detects a maximum position of the sensor output signal, and then supplies the detected maximum position as a peak detection signal to the sample and hold circuit 22, and also to the control unit. Since this peak detecting circuit 22 is employed so as to detect the maximum position of the sensor output signal, a center position of the image forming position adjusting-purpose reference pattern image along the width direction can be detected. Then, the control unit calculates an image forming position based upon this peak detection signal, and thus, adjusts the position forming position.

The sample and hold circuit 22 holds the sensor output signal outputted from the AMP 20, while using the peak detection signal outputted from the peak detecting circuit 21 as a trigger signal. As a result, the maximum value of the sensor output signal is holded, and then, this signal is outputted as a hold signal to the control unit. In this control unit, image density is calculated based upon the hold signal of this maximum value, and thus, the image density is controlled.

The under peak detecting circuit 23 detects a minimum position of the sensor output signal, and then, supplies the detection signal as an under peak detection signal to the sample and hold circuit 24. The sample and hold circuit 22 holds the sensor output signal outputted from the AMP 20, while using the under peak detection signal outputted from the under peak detecting circuit 23 as a trigger signal. As a result, the minimum value of the sensor output signal is holded, and then, this signal is outputted as an under peak hold signal to the control unit. In this control unit, image density is calculated based upon the hold signal of this minimum value, and thus, the image density is controlled. It should be understood that the AMP 20, the peak detecting circuit 21, the under peak detecting circuit 23, the sample and hold circuits 22 and 24 may be realized by applying thereto general-purpose electronic circuits, and therefore, explanations thereof are omitted.

Figure 6:
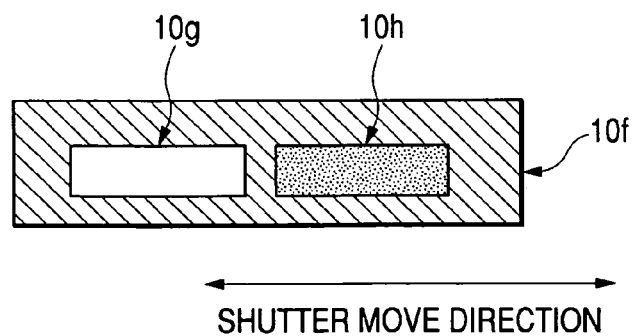
FIG. 6 is a structural diagram of a shutter.

In order to detect density of a reference pattern image based upon an output signal derived from the photodiode 10d, an output signal detected from the reference pattern image must be compared with an output signal which constitutes a reference. To this end, such a unit is required which is capable of switching a case that the reference light is entered to the photodiode 10d, and another case that the reflection light reflected from the reference pattern image is entered to the photodiode 10d. As a result, a shutter 10f is mounted on the photosensor 10 in such a manner that this shutter 10f can be slid (FIG. 6). This drawing corresponds to a plan view for viewing the shutter 10f from the LED side Both a measuring window 10g and a reference plate 10h used to obtain a reference as to an output voltage of a sensor are mounted on this shutter 10f. This shutter 10f is equipped with a mechanism which is transported by a drive apparatus (not shown) along a direction indicated by an arrow of FIG. 6 in response to reflection light which is entered to the photodiode 10d. The shutter 10f is positioned in such a manner that the reference plate 10h is arranged on the optical axis of the light receiving system under the normal closed condition. Only when a reference pattern image is measured, the shutter 10f is transported in such a manner that the shutter 10f is opened and the measuring window 10g is arranged on the optical axis of the light receiving system.

Figure 7:
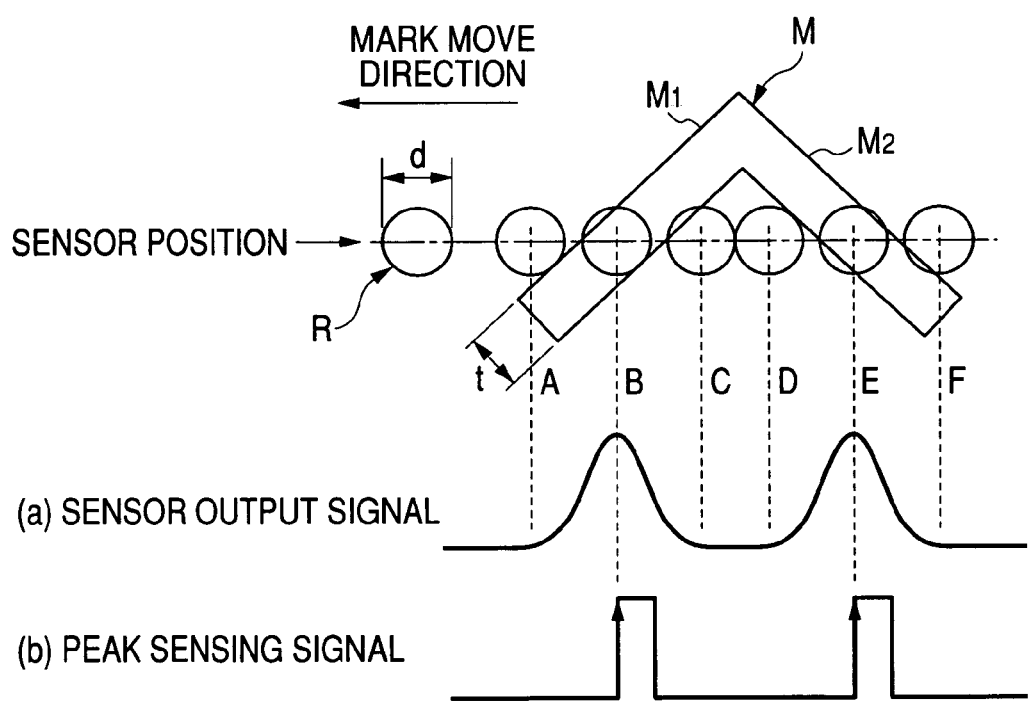
FIG. 7 is a diagram for representing a positional relationship between a visual field of a photosensor on an intermediate transfer member belt and the image forming position adjusting-purpose reference pattern, and changes in sensor output signals and peak sensing signals at this time.

FIG. 7 indicates a positional relationship between the image forming position adjusting-purpose reference pattern image M formed on the intermediate transfer member belt 6 and the visual field region R on the intermediate transfer member belt 6 of the photosensor 10 in accordance with a time elapse. A lower graph (a) in FIG. 7 indicates a waveform of a sensor output signal corresponding to a position of the visual field region R of the photosensor 10, and the lowermost graph (b) in FIG. 7 shows a peak sensing signal of the image forming position adjusting-purpose reference pattern image M which is outputted from the peak detecting circuit. In this case, a controlling mark M is formed in such a manner that a width t of each of edges M1 and M2 is not made equal to, but slightly smaller than the diameter "d (1 mm)" of the visual field region R.

The image forming position adjusting-purpose reference pattern image M which has been primary-transferred to the intermediate transfer member belt 6 passes through the front surface of the photosensor 10 in connection with the rotation of this intermediate transfer member belt 6, and then, intersects the visual field region R of the photosensor 10. When the image forming position adjusting-purpose reference pattern image M is moved in connection with the intermediate transfer member belt 6 and the visual field region R of the photosensor 10 is reached to a point A on the intermediate transfer belt 6, since one edge M1 of the image forming position adjusting-purpose reference pattern image M is entered into this visual field region R, the sensor output signal starts to be changed. Furthermore, when the image forming position adjusting-purpose reference pattern image M is moved, an area of the image forming position adjusting-purpose reference pattern M which is contained in the visual field region R, namely, an overlapped area between the visual field region R and one edge M1 of the image forming position adjusting-purpose reference pattern M is enlarged, so that the sensor output signal is gradually increased, and the sensor output signal becomes maximum at such a point B where the visual field region R is substantially covered by the image forming position adjusting-purpose pattern M.

As previously explained, since the width t of each of the edges M1 and M2 of the image forming position adjusting-purpose reference pattern image M is made slightly smaller than the diameter d of the visual field region R of the photosensor 10, when the image forming position adjusting-purpose reference pattern image M passes through a point B, an area of the image forming position adjusting-purpose reference pattern M which is contained in the visual field region R, namely, an overlapped area between the visual field region R and the image forming position adjusting-purpose reference pattern M is decreased, so that the sensor output signal is gradually decreased, and then, a sensor output signal becomes minimum at such a point where the image forming position adjusting-purpose reference pattern image M is completely escaped from the visual field region R of the photosensor 10 (point C).

As previously explained, in the example shown in FIG. 7, while one edge M1 of the image forming position adjusting-purpose reference pattern image M passes through the visual field region R of the photosensor 10 (namely, between point A and point B), the overlapped area between this visual field region R and the controlling mask M is continuously changed in connection with the travel of the intermediate transfer member belt 6, and thus, the image forming apparatus is arranged in such a manner that the sensor output signals having the same strengths are not continued to be outputted from the photosensor 10. In other words, as to the sensor output signals, the maximum value is instantaneously produced. The waveform of such a sensor output signal may be readily obtained by that the visual field region R of the photosensor 10 is formed as a circular shape, and furthermore, the width of the image forming position adjusting-purpose reference pattern image M is made equal to, or smaller than the diameter of the visual field region R.

In a multi-color printing machine, a color copying machine, a color printer and the like, when the image forming position adjusting-purpose reference pattern image M is formed on a moving member such as an intermediate transfer member belt, there is a certain case that the width of the image forming position adjusting-purpose reference pattern image M is changed, depending upon such an environmental condition as a temperature and a humidity at this time, and thus, it is practically difficult to make such an image forming position adjusting-purpose reference pattern image M having the width completely equal to the diameter of the visual field region R of the photosensor 10. As a consequence, as previously explained, even in such a case that the width of the image forming position adjusting-purpose reference pattern images M is smaller than the diameter of the visual field region R, such a condition that the instantaneous maximum value is produced in the waveform of the sensor output signal becomes advantageous when the color printer and the like are actually constructed.

As indicated in FIG. 7, in the case that an instantaneous maximum value is produced in the waveform of the sensor output signal, this maximum value is produced when a center position (gravity position) of one edge M1 of the image forming position adjusting-purpose reference pattern image M along the width direction is made coincident with the center position of the visual field region R or the photosensor 10. As a result, if such an arrangement is constructed that the maximum value (peak value) of the sensor output signal is sensed by the peak sensing circuit, and, as indicated in the graph (b) in FIG. 7, a pulse-shaped peak sensing signal is outputted in correspondence with this maximum value, a rising edge portion of this pulse-shaped peak sensing signal indicates the center position (gravity position) of one edge M1 of the image forming position adjusting-purpose reference pattern image M, so that the position of this one edge M1 can be correctly detected.

Also, the image forming position adjusting-purpose reference pattern image M, which is shown in FIG. 3A and FIG. 7, is formed in a V shape and owns the two edges M1 and M2 which are inclined at substantially 45 degrees along such a direction different from the transport direction of the intermediate transfer member belt 6. As a result, since a single set of this image forming position adjusting-purpose reference pattern image M is detected by the photosensor 10 of this embodiment, both a positional shift amount along the main scanning direction and another positional shift amount along the sub-scanning direction can be grasped at the same time. That is to say, although the sensor signal once become minimum since the visual field region R is reached to the point C, if this visual field region R passes through the point D, the sensor signal again starts to rise, because the edge M2 of the image forming position adjusting-purpose reference pattern image M starts to be overlapped with the visual field region R. Then, the sensor output signal represents the maximum value at such a point E where the center position of the edge M2 along the width direction is overlapped with the center position of the visual field region R. Then, in connection with such a condition that the overlapped area between the edge M2 and the visual field region R is decreased, the sensor output signal is also decreased, and is returned to the minimum output at a point F where the image forming position adjusting-purpose reference pattern image M is escaped from the visual field region R.

As a consequence, when the image forming position adjusting-purpose reference pattern image M having the V-shape shown in FIG. 3A is read, as represented in the graph (b) in FIG. 7, one pair of pulse-shaped peak detecting signals may be outputted from the peak detecting circuits in correspondence with both the point B and the point E where the center positions (gravity positions) of the respective edges M1 and M2 of the image forming position adjusting-purpose reference pattern image M are overlapped with the center position of the visual field region R.

Figure 8:
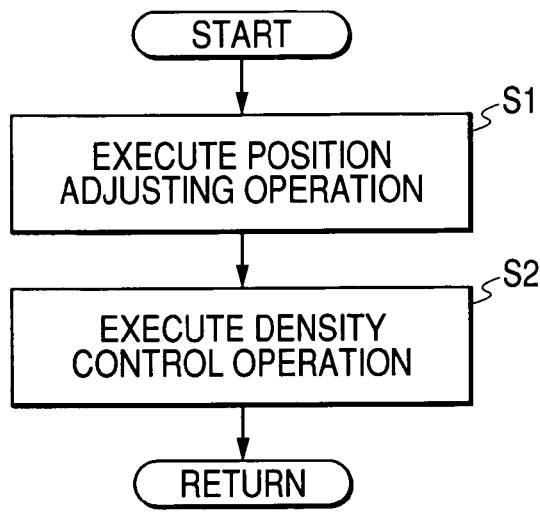
FIG. 8 is a flow chart for describing an entire control operation.

The control operations of this embodiment, namely both the output image position adjusting operation and the output image density control operation may be represented by such a flow chart of FIG. 8. First, in a step S1, the output image position adjusting operation is carried out. Next, at a step S2, the output image density control operation is carried out. It should be understood that both the position adjusting operation and the density control operation may be always carried out in the sequential manner as indicated in this flow chart. Alternatively, the position adjusting operation and the density control operation may be carried out at different timing.

Subsequently, the output image position adjusting operation in this embodiment may be indicated as such a flow chart shown in FIG. 9. First, in a step S11, the image position adjusting-purpose reference pattern image M indicated in FIG. 3A is formed on the intermediate transfer member belt 6. In the next step S13, the control unit 100 measures and calculates an absolute value positional shift amount of the reference cyan color with respect to a target value of the reference cyan color along the main scanning direction, and also, relative positional shift amounts of yellow and magenta colors with respect to the reference cyan color based upon a peak detection signal outputted from the photosensor 10.

Figure 10:
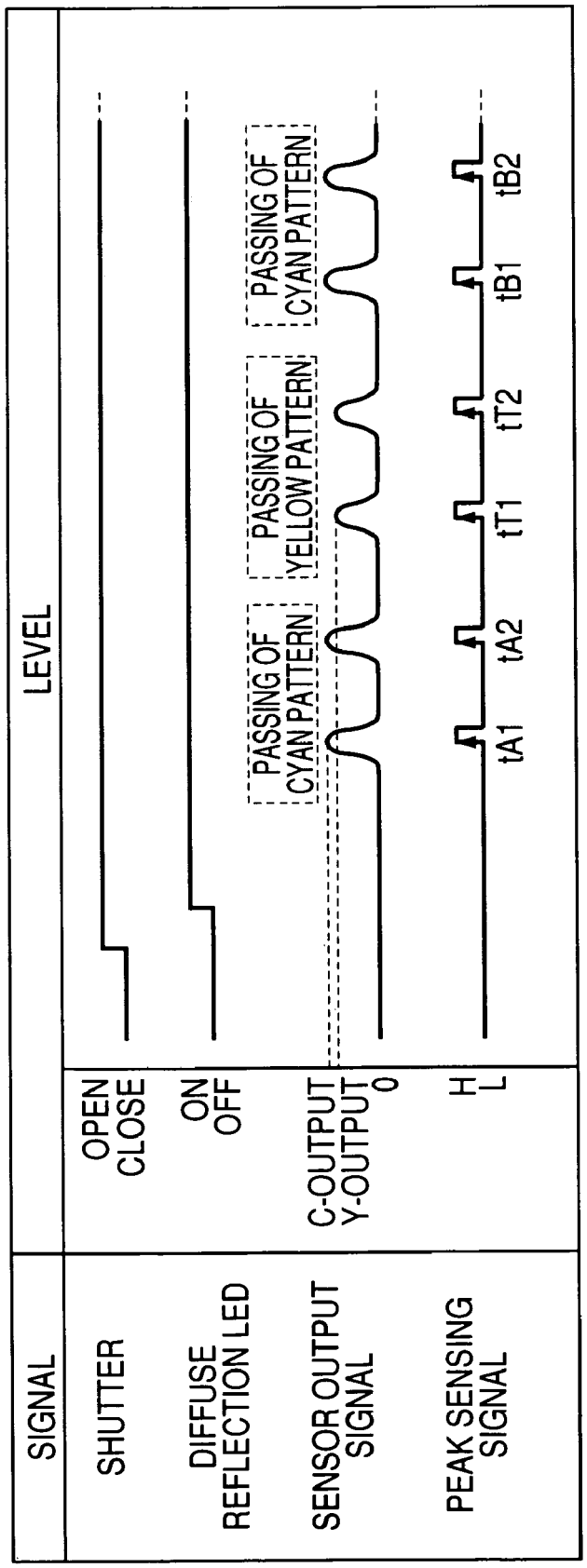
FIG. 10 is a timing chart for indicating timing when the image position adjusting-purpose reference pattern is measured.

In this embodiment, a positional shift amount of a reference pattern image is obtained by executing a calculation from a timing chart shown in FIG. 10 when the reference pattern image is measured. In FIG. 10, there are shown: a waveform of an operating signal of the shutter 10f of the photosensor 10, a waveform of an ignition signal of the diffuse LED 10b of the photosensor 10, a waveform of a sensor output signal thereof, and a waveform of a peak detection signal thereof in this order from the upper portion.

As indicated in FIG. 10, a measuring operation as to a positional shift amount is firstly commenced from such a condition that the shutter 10f is closed and the LED is turned OFF. Before the reference pattern passes through a measuring position of the photosensor, the shutter 10f is opened, and thereafter, the diffuse LED 10b is turned ON. At this time, a sensor output signal becomes 0 V. This fact is revealed from the following reason. That is, since the surface of the intermediate transfer member belt 6 used in this embodiment is colored in black and owns either a mirror plane or gloss, and further, the illumination light of the diffuse LED 10b is not substantially diffused on a non-image portion of the surface of the intermediate transfer member belt 6, the sensor output signal becomes 0 V.

Under such a condition that the shutter 10f is kept opened, since one edge of the cyan-colored reference pattern image passes through the measuring position of the photosensor 10, an output signal of this photosensor 10 owns a pulse-shaped waveform in correspondence with a toner amount of this cyan color. In this case, as indicated in FIG. 5, the peak detecting circuit 21 detects a maximum value of the sensor output signal, and thus, outputs a peak detection signal. In this case, it is so assumed that a time instant is "tA1" which is defined after the positional shift measuring operation is commenced until the peak detection signal is outputted. Then, another time instant is assumed as "tA2" from the commencement of the positional shift measuring operation until the peak detection signal detected by the peak detecting circuit 21 is outputted since the remaining one edge of the reference pattern image passes through the measuring position.

Subsequently, time instants "tT1", "tT2", "tB1", and "tB2" are sequentially measured in a similar measuring manner, which are defined until peak output signals are outputted in connection with such an operation that the yellow reference pattern image, the cyan reference pattern image, the magenta reference pattern image, the magenta reference pattern image, the cyan reference pattern image, the black reference pattern image pass through the measuring point of the photosensor 10. It should also be noted that FIG. 10 represents such a condition that the cyan, yellow, and cyan reference pattern images pass through the measuring point of the photosensor 10. Thereafter, after all of the reference pattern images have passed through the measuring point of the photosensor 10, the shutter 10f is closed and the diffuse LED 10b is turned OFF. As a consequence, the simple measuring operation of the reference pattern images is accomplished.

Next, the calculation of the image forming position is carried out by calculating an absolute value positional shift amount of the reference cyan color with respect to a target value thereof along the main scanning direction, and relative positional shift amounts of yellow and magenta colors with respect to the reference cyan color. First, the absolute value positional shift amount of the reference cyan color along the main scanning direction may be calculated as follows: Absolute value positional shift amount along main scanning direction=[(tA2−tA1)−target value]/2.

The relative positional shift of yellow with respect to the reference cyan color may be calculated as follows:

Positional shift along sub-scanning direction=$[tT2+tT1)/2-((tA2+tA1)/2+(tB2+tB1)/2)/2] \times PS = [(tT2+tT1)/2-(tA2+tA1)/4-(tB2+tB1)/4] \times PS$ Positional shift along main scanning direction= $[((tB1+tA1)/2-tT1+\text{error along sub-scanning direction}+tT2-(tB2+tA2)/2-\text{error along sub-scanning direction})/2] \times PS = [((tB1+tA1)/2-tT1+tT2-(tB2+tA2)/2)/2] \times PS$ In the formulae, symbols tA1, tA2, tT1, tT2, tB1, and tB2 represent time instants (µs) defined from starting of the positional shift measuring operation until the peak signals are outputted. Symbol "PS" shows a process speed (mm/s) Both a positional shift of magenta and a positional shift of black with respect to the reference cyan color may be calculated in a similar manner.

Figure 9:
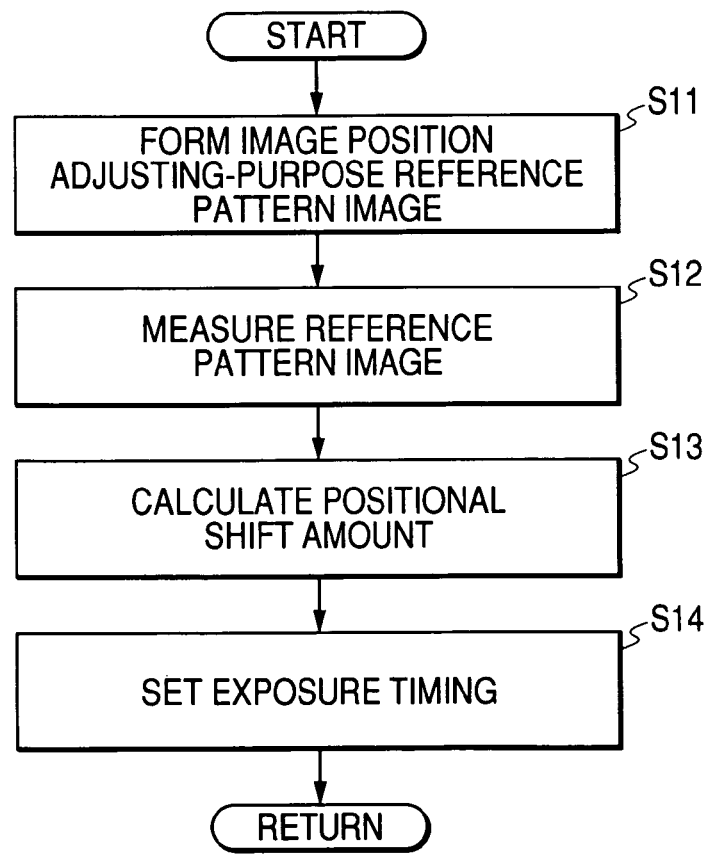
FIG. 9 is a flow chart for describing an image position adjusting operation.

This calculation corresponds to a process operation of a step S13 shown in FIG. 9. After the control unit 100 has measured the positional shift amount and the calculation operation, the control unit 100 sets an image forming position when an output image is formed in a step S14 of FIG. 9. In other words, the control unit 100 sets exposing timing along the main scanning direction and the sub-scanning direction by the ROS. Since a series of these process operations are carried out, a single set of output image position adjusting operation is accomplished.

Figure 11:
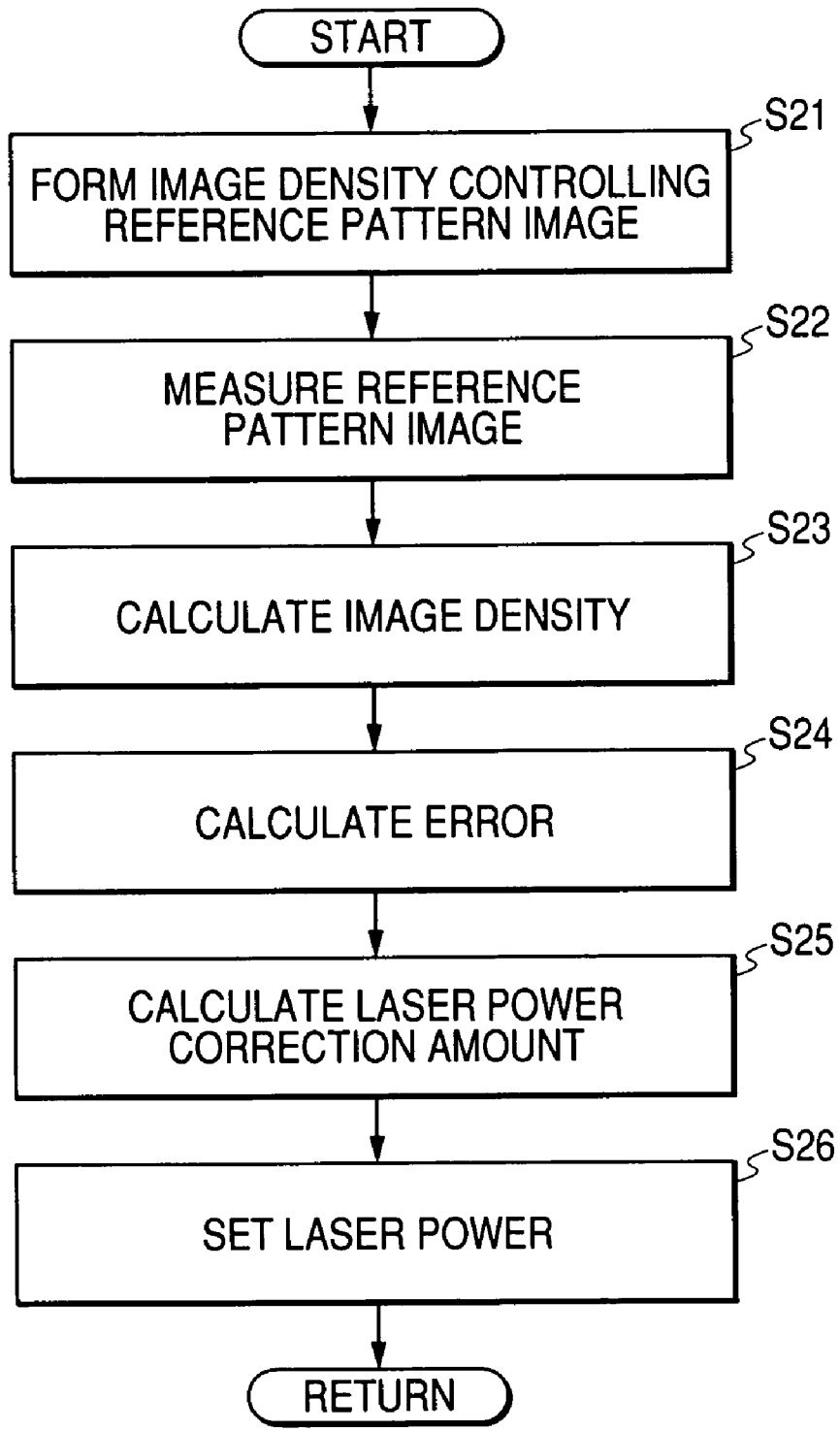
FIG. 11 is a flow chart for explaining an image density control operation.

A flow chart for explaining the image density control operation according to this embodiment is shown in FIG. 11. First, in a step S21, the image density control reference pattern image D shown in FIG. 3B is formed on the intermediate transfer belt 6. Next, in a step S22, the reference pattern is measured by the photosensor 10. Thereafter, in a step S23, the control unit 100 calculates image density of the reference pattern image from a hold signal outputted from the detecting unit.

Figure 12:
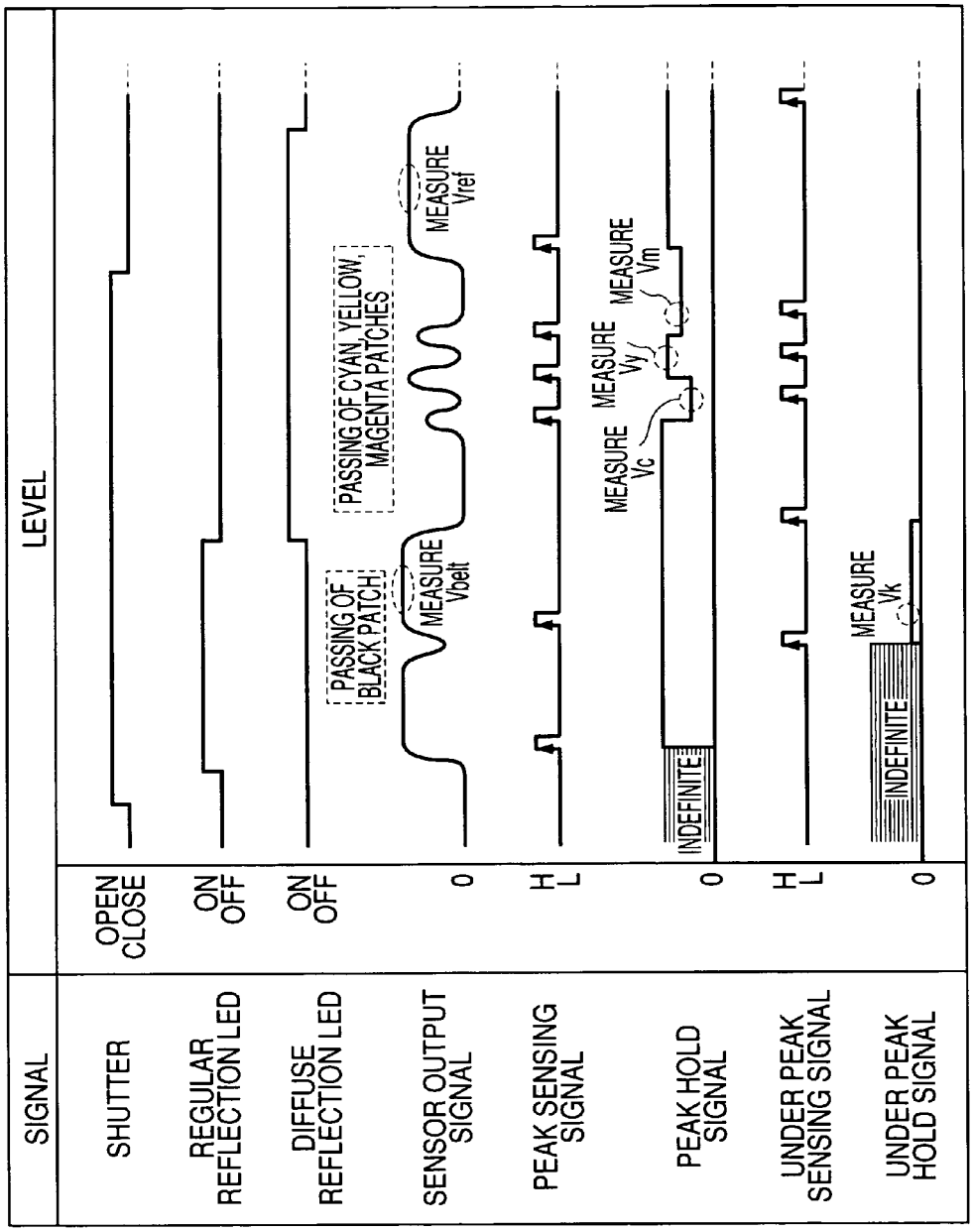
FIG. 12 is a timing chart for indicating timing when the image density controlling reference pattern is measured.

A density measurement of the reference pattern is carried out by way of a calculation from a timing chart shown in FIG. 12 when the density controlling reference pattern is measured. In FIG. 12, various waveforms are represented, namely, a waveform of an operating signal of the shutter 10$f$ of the photosensor 10, a waveform of a turn-ON signal of the regular reflection LED 10$a$ of the photosensor 10, a waveform of a turn-ON signal of the diffuse LED 10$b$ thereof; a waveform of a sensor output signal; a waveform of a peak detection signal; a waveform of a peak hold signal, a waveform of an under peak detection signal, and a waveform of an under peak hold signal in this order from an upper portion thereof.

As indicated in FIG. 12, density measuring operation is commenced under such a condition that the shutter 10$f$ is firstly closed, and both the regular reflection LED 10$a$ and the diffuse reflection LED 10$b$ are turned OFF. The shutter 10$f$ is opened before the reference pattern image passes through the measuring position of the photosensor 10, and thereafter, the regular reflection LED 10$a$ is turned ON. At this time, a sensor output signal is outputted from the photosensor 10, which has a voltage value in response to a light amount of regular reflection light reflected from the intermediate transfer belt 6. Thereafter, since the black reference pattern image passes through the measuring position, an output voltage of the photosensor 10 owns a pulse-shaped waveform which is decreased in correspondence with a toner amount of the black color. At this time, as shown in FIG. 5, the under peak detecting circuit 23 detects a minimum value of the sensor output signal and thus outputs an under peak detection signal. When the sample and hold circuit 24 employs as a trigger a rising pulse of the under peak detection signal which is outputted from the under peak detecting circuit 23, the sample and hold circuit 24 holds the minimum value of the sensor output signal in correspondence with the toner amount of the black color, so that a density voltage "Vk" of the black color is measured. Next, after the black reference pattern image has passed through the measuring position, a sensor output signal again represents such a voltage value in response to a light amount of regular reflection light reflected from the intermediate transfer member belt 6, and then, this voltage value is measured as a belt surface voltage (Vbelt). Then, after this belt surface voltage has been measured, the regular reflection LED 10$a$ is turned OFF, and the diffuse LED 10$b$ is turned ON, so that a sensor output signal becomes zero V.

Thereafter, since the cyan reference pattern image passes through the measuring position, a sensor output signal of the photosensor 10 owns a pulse-shaped waveform in correspondence with a cyan toner amount. At this time, the while the sample and hold circuit 22 employs as a trigger a rising pulse of the under peak detection signal which is outputted from the peak detecting circuit 21, the sample and hold circuit 22 holds a maximum value of the sensor output signal in correspondence with the toner amount of the cyan color, so that a density voltage (Vc) of the cyan color is measured. Subsequently, since the yellow reference pattern image and the magenta reference pattern image pass through the measuring point, a density voltage (Vy) of the yellow color and a density voltage (Vm) of the magenta color are measured.

After all of the reference pattern images have passed through the measuring position, the shutter 10$f$ is closed. As a consequence, as a sensor output signal, such a voltage value is outputted in correspondence with reflection light reflected from the reference plate 10$h$ of the shutter 10$f$, and thus, this voltage value is measured as a reference output voltage (Vref) of the photosensor 10. Thereafter, the diffuse LED 10$b$ is turned OFF, so that a single set of the reference pattern image measuring operation is accomplished.

With respect to image destination calculations, a calculating method thereof for a black color is different from a calculating method for a color (CYM). The black image density is calculated in such a manner that a relative value of image density with respect to the non-image plane of the intermediate transfer member belt 6 is defined as follows:

Image density: $Dk = Vk/Vbelt$.

In contrast, the image density of the color (CYM) is calculated in such a manner that a relative value of image density with respect to the output of the reference plate 10$h$ is defined as follows:

Image density: $Dn = ((Vn \text{ average value})/Vref)$ note that n=toner color (c, y, m).

As previously explained, the reason why the relative value with respect to the sensor output of either the surface of the intermediate transfer member belt 6 or the reference plate 10$h$ is employed as the image density is given as follows. That is, even when the LED light amount and the PD sensitivity are varied due to contamination of the sensor, aging effects, and the temperature changes, the image density of the reference pattern is measured in high precision. In a step S23 of FIG. 11, the image density of the reference pattern image is calculated in the above-described manner. In a step S24, a calculation is made of an error between a predetermined density target value and the calculated image density.

A correction amount: $\Delta LP$ of the ROS laser power in a step S25 of FIG. 11 may be calculated as follows:

Correction amount of laser power: $\Delta LP = \Delta Dn/An$, note that n=toner color (k, c, y, m).

In this formula, symbol "$\Delta Dn$" indicates the density error of the reference pattern, and symbol "An" shows a coefficient indicative of a correspondence relationship between the laser power and the image density of the reference pattern. This coefficient is previously acquired by way of an experiment, or the like.

Next, in a step S26, the correction amount: $\Delta LP$ of the laser power calculated in the step S25 is subtracted from the laser power when the reference pattern image is formed in order to correct the set value of the laser power. The laser power set value obtained in this step is supplied to the ROS 3 as laser power when the output image is formed. Since the above-described operations are carried out, a single set of the output image density controlling operation is ended. As previously explained, since both the output image position adjusting operation and the output image density control operation are repeatedly carried out in a periodic manner, both the image forming position and the output image density can be kept constant.

As previously explained, in accordance with the photosensor 10 of the present embodiment, the light receiving subject region for the regular reflection light and the light receiving subject region for the diffuse reflection light can be made equal to each other in the photodiode 10d. As a result, the reference pattern images for the yellow, magenta, cyan colors, which reflect the diffuse reflection light are no longer set to be large, as set in the conventional technique. Even when the small reference pattern image is employed, the reflection light thereof can be received by the photodiode 10d, so that the toner amounts used to form the above-explained reference pattern images can be reduced. Also, since the regular reflection-purpose LED 10a and the diffuse reflection-purpose LED 10b are arranged at the positions where both the regular reflection light and the diffuse reflection light are entered to the photodiode 10d, such a photosensor apparatus having both the density sensor function and the position sensing sensor by employing a single light receiving element can be constructed, and thus, the apparatus can be made compact in low cost.

In the above-explained embodiment, such a type of color electrophotographic system has been described. That is, the IOT is equipped with the xerography engines for the yellow, magenta, cyan, and black colors, which are arranged by the photosensitive members, the contact changing devices, the ROSs, and the developing devices. After the toner images formed on the photosensitive members are primary-transferred onto the intermediate transfer member belt, these toner images are transferred to the paper so as to be fixed. However, the application range of the present invention is not limited only this embodiment. For instance, a similar effect may be achieved even in such a type of image forming apparatus in which a paper transport belt is employed instead of an intermediate transfer member belt, and toner images on photosensitive members are directly transferred to a paper transported by the paper transport belt. Alternatively, the similar effect may be achieved in such a type of image forming apparatus that respective color toner images are overlapped with each other on a belt-shaped, or a drum-shaped photosensitive member by using charging devices, exposing devices, and developing devices, which are provided around to photosensitive member and exclusively used for the respective colors. Also, the exposing apparatus is not limited only to the ROS, but may be replaced by a device using a LED array.

Also, in the above-described embodiment, the measuring position of the reference pattern image is set on the intermediate transfer member belt. Alternatively, this measuring position may be set even on the photosensitive member, even on the paper transport belt, or even on the paper in accordance with the structures of the image forming apparatus. Then, in accordance with a measuring place, the structure of the detecting unit may be changed, for example, a CCD, a CMOS image sensor, or the like may be employed.

Further, as to a photosensor, while not only one photosensor, or but also plural photosensors may be alterntively arranged along the main scanning direction, such a photosensor arrangement may be constructed which may correct a magnification shift along the main scanning direction, and a skew shift under which an image formed on an intermediate transfer member belt owns a certain inclination.

Furthermore, as the adjusting amount for the output image density control, not only the laser power set value is employed, but also any other adjusting amount may be employed, if this adjusting amount can adjust the output image quality. For example, a charging voltage setting value of a charging device, a developing bias setting value, a toner supply amount, a coefficient of a conversion table for an input image signal may be alternatively employed. Also, plural sets of these operation amounts may be used so as to control the image quality.

The image density controlling reference pattern image is not limited only to one sort of pattern image (mesh point coverage: 60%), may be realized by employing two, or more sorts of patterns having different Cin values, while Cin values may be arbitrarily selected in correspondence with an image forming apparatus. Also, the size of the reference pattern image is not limited only to the sizes described in the embodiment, but may be alternatively changed in correspondence with a registration shift amount conceivable in an image forming apparatus.

Then, the shape of the reference pattern image is not limited only to the V-shaped pattern. Alternatively, while a band-shaped pattern extended along the main scanning direction is employed, this belt-shaped pattern may be used so as to detect both image density and a position along the sub-scanning direction. Since such a belt-shaped pattern is employed, the length of the reference pattern image may be furthermore made shorter along the sub-scanning direction. Otherwise, the known patterns other than this belt-shaped pattern may be employed. Furthermore, while two sorts, or more sorts of adjusting modes such as a coarse adjusting mode and a fine adjusting mode are provided, sizes of reference patterns may be alternatively switched in response to an adjusting mode.

What is claimed is:

1. A photosensor apparatus comprising:
    a light receiving element that receives reflection light of light which is illuminated onto a reference pattern image formed on a moving member;
    a first illuminating unit that is disposed at a first position so that regular reflection light of light from the first illuminating unit by the reference pattern image enters to the light receiving element;
    a second illuminating unit that is disposed at a second position so that diffuse reflection light of light from the second illuminating unit by the reference pattern image enters to the light receiving element; and
    a light receiving optical system that conducts the regular reflection light and the diffuse reflection light generated at the reference pattern image to the light receiving element,
    wherein the light receiving optical system includes a lens; constitutes an image forming optical system that focuses the reference pattern image on a light receiving plane of the light receiving element with respect to the diffuse reflection light; and enters only a part of regular reflection light to the light receiving plane of the light receiving element with respect to the regular reflection light, the part of regular reflection light being reflected from substantially the same region where the diffuse reflection light is received by the light receiving element within the reference pattern image on the moving member.

2. The photosensor apparatus as claimed in claim 1,
    wherein an image forming magnification of the image forming optical system corresponds to an equivalent magnification.

3. The photosensor apparatus as claimed in claim 1,
wherein a mask is provided before the light receiving element, the mask restricting a visual field region of the light receiving plane of the light receiving element.

4. A color image forming apparatus that senses a density and a position of reference pattern images being made in a plurality of colors and formed on an image carrier; adjusts an image density; and positions the reference pattern images of respective colors with each other based on a sensing result, the color image forming apparatus comprising:
a photosensor apparatus as a unit that senses the reference pattern images,
wherein the photosensor apparatus includes:
a light receiving element that receives reflection light of light which is illuminated onto the reference pattern image formed on a moving member;
a first illuminating unit that is disposed at a first position so that regular reflection light of light from the first illuminating unit by the reference pattern image enters to the light receiving element;
a second illuminating unit that is disposed at a second position so that diffuse reflection light of light from the second illuminating unit by the reference pattern image enters to the light receiving element; and
a light receiving optical system that conducts the regular reflection light and the diffuse reflection light generated at the reference pattern image to the light receiving element, and
wherein the light receiving optical system includes a lens; constitutes an image forming optical system that focuses the reference pattern image on a light receiving plane of the light receiving element with respect to the diffuse reflection light; and enters only a part of regular reflection light to the light receiving plane of the light receiving element with respect to the regular reflection light, the part of regular reflection light being reflected from substantially the same region where the diffuse reflection light is received by the light receiving element within the reference pattern image on the moving member.

5. The color image forming apparatus as claimed in claim 4,
wherein an image forming magnification of the image forming optical system corresponds to an equivalent magnification.

6. The color image forming apparatus as claimed in claim 4,
wherein a mask is provided before the light receiving element, the mask restricting a visual field region of the light receiving plane of the light receiving element.

7. The color image forming apparatus as claimed in claim 4,
wherein a maximum position of a signal output from the photosensor apparatus is detected.

8. The color image forming apparatus as claimed in claim 7,
wherein an image forming position adjusting-purpose reference pattern image is positioned by detecting the maximum position of the signal output from the photosensor apparatus.

9. The color image forming apparatus as claimed in claim 4,
wherein a minimum position of a signal output from the photosensor apparatus is detected.

10. The color image forming apparatus as claimed in claim 9,
wherein the image density is controlled by detecting the minimum position of the signal output from the photosensor apparatus.

11. The color image forming apparatus as claimed in claim 4 further comprising:
a switching unit that switches a reference light to the light receiving element and the reflection light reflected from the reference pattern image.

12. The color image forming apparatus as claimed in claim 11,
wherein the switching unit is a shutter which is slidably mounted on the photosensor apparatus.

13. The color image forming apparatus as claimed in claim 4,
wherein as to a signal output from the photosensor apparatus a maximum value is instantaneously produced.

14. The color image forming apparatus as claimed in claim 4,
wherein an image forming position is obtained from an absolute value positional shift amount of a reference color with respect to a target value thereof along a main scanning direction and a relative positional shift amount of other color with respect to the reference color.

15. The color image forming apparatus as claimed in claim 4,
wherein a relative value with respect to an output of either a surface of an intermediate transfer member belt or a reference plate is employed as the image density.

16. A photosensing method comprising:
disposing a first illuminating unit at a first position so that regular reflection light of light from the first illuminating unit by a reference pattern image enters to a light receiving element;
disposing a second illuminating unit at a second position so that diffuse reflection light of light from the second illuminating unit by the reference pattern image enters to the light receiving element;
focusing the reference pattern image on a light receiving plane of the light receiving element with respect to the diffuse reflection light; and
entering only a part of regular reflection light to the light receiving plane of the light receiving element with respect to the regular reflection light, the part of regular reflection light being reflected from substantially the same region where the diffuse reflection light is received by the light receiving element within the reference pattern image on the moving member.

* * * * *